United States Patent [19]

Callahan et al.

[11] Patent Number: 4,622,424

[45] Date of Patent: Nov. 11, 1986

[54] PREPARATION OF ACRYLIC ACID AND METHACRYLIC ACID IN A COMBINATION FIXED-FLUID BED REACTOR

[75] Inventors: James L. Callahan, Wooster; Arthur F. Miller; Wilfrid G. Shaw, both of Lyndhurst, all of Ohio

[73] Assignee: The Standard Oil Company, Cleveland, Ohio

[21] Appl. No.: 773,145

[22] Filed: Sep. 6, 1985

Related U.S. Application Data

[60] Continuation of Ser. No. 729,446, May 1, 1985, abandoned, which is a continuation of Ser. No. 605,046, Apr. 30, 1984, abandoned, which is a division of Ser. No. 108,868, Dec. 31, 1979, Pat. No. 4,470,931, which is a division of Ser. No. 954,262, Oct. 24, 1978, abandoned.

[51] Int. Cl.$^4$ .................... C07C 51/25; C07C 57/05
[52] U.S. Cl. .................... 562/545; 422/139; 422/141; 549/258; 560/208; 562/546; 562/547; 568/476; 568/479; 568/480

[58] Field of Search .................... 562/546, 547, 545; 422/141, 139

[56] References Cited

U.S. PATENT DOCUMENTS

| | | | |
|---|---|---|---|
| 3,374,052 | 3/1968 | Fan et al. | 423/653 |
| 3,472,892 | 10/1969 | Callahan et al. | 260/465.3 |
| 3,639,103 | 2/1972 | Sheely | 260/465.3 |
| 3,819,679 | 6/1974 | Sheely | 260/465.3 |
| 3,944,592 | 3/1976 | Sheely | 260/465.3 |

*Primary Examiner*—Vivian Garner
*Attorney, Agent, or Firm*—Charles S. Lynch; John E. Miller; Larry W. Evans

[57] ABSTRACT

A process for conducting a combination of fixed and fluid-bed catalytic reactions is achieved by employing fixed-bed catalysts on supports within the fluid bed. The fluid-bed catalysts may move in both directions through the fixed bed, thereby giving advantages of both types of beds in one reactor.

2 Claims, 1 Drawing Figure

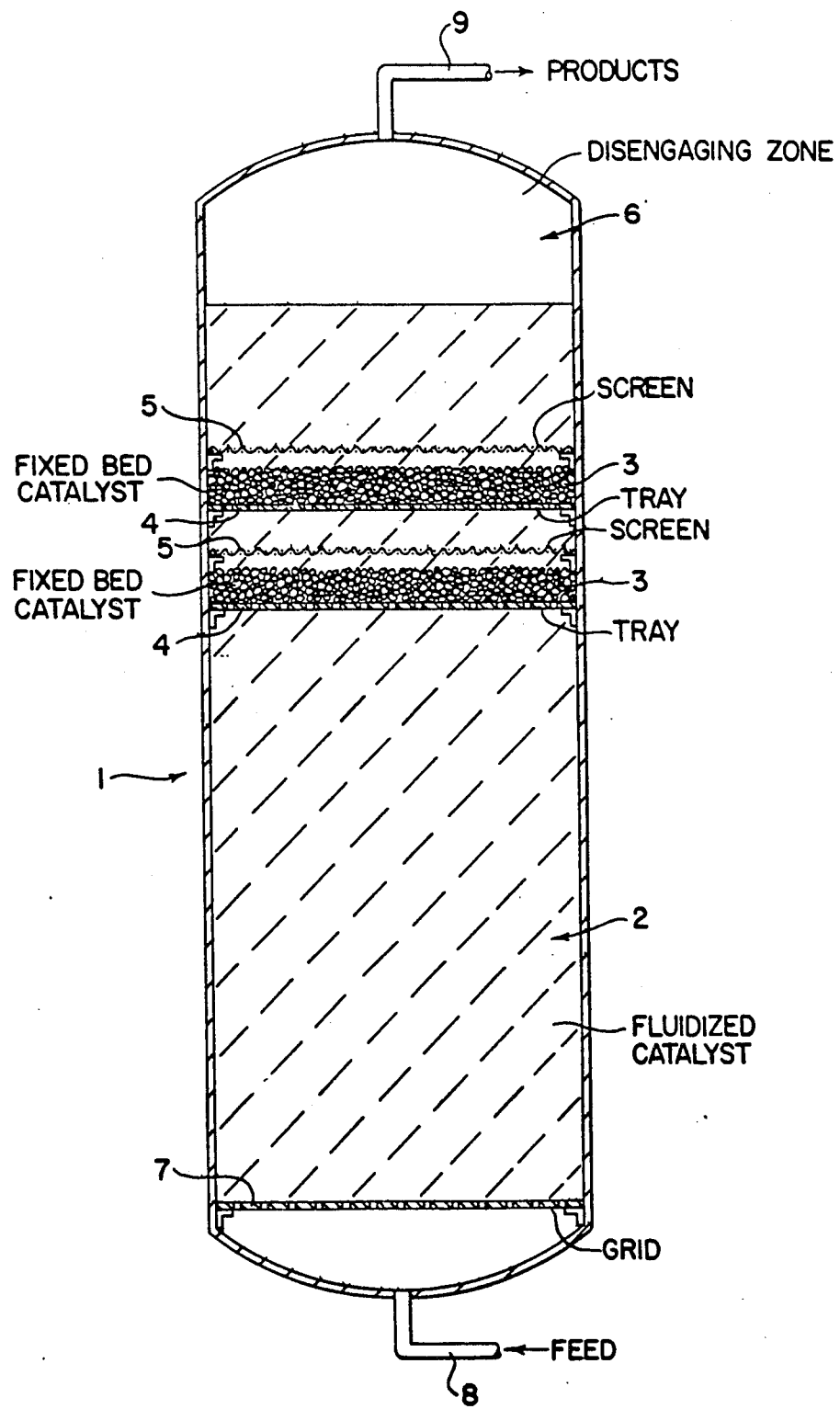

PREPARATION OF ACRYLIC ACID AND METHACRYLIC ACID IN A COMBINATION FIXED-FLUID BED REACTOR

This application is a continuation of Ser. No. 729,446, filed May 1, 1985 abandoned, which is a continuation of Ser. No. 605,046, filed Apr. 30, 1984 abandoned, which is a divisional of co-pending application Ser. No. 108,868, filed Dec. 31, 1979, now U.S. Pat. No. 4,470,931, issued Sept. 11, 1984, which is a divisional of application Ser. No. 954,262, filed Oct. 24, 1978, now abandoned.

BACKGROUND OF THE INVENTION

Attempts to combine fixed and fluid-bed catalytic reactions in one bed have been made previously. U.S. Pat. No. 3,374,052 discloses a vessel with a movable top plate that closes in on the top of the fluid bed. This pressure from the plate renders the top of the bed non-fluidized, or fixed. This method, however, would be difficult to apply to a chemical reaction involving more than one type of catalyst in the same reactor, and this fixed-bed section is not interspersed throughout the fluid catalyst bed, resulting in disadvantages such as heat transfer capabilities.

The fact that catalysts may be of fixed or fluid type is known in the art.

The selection of the type of bed for a given reaction is dependent on several factors. Fixed-bed reactors tend to provide excellent gas solids contacting, less catalyst than for a fluid bed, and a smaller reactor. Fixed-bed reactors also allow the grading of catalyst within the reactor, and different types of catalyst may be installed at different locations. However, in reactions in which there is a large amount of heat released or absorbed, fixed-bed reactors require a large amount of heat transfer surface to adequately control the reaction temperature. The fixed-bed particles are normally much larger than fluid-bed particles, and therefore are more sensitive to reactant diffusion complications. Finally, fixed-bed reactors generally require efficient mixing of all reactants prior to entering the catalyst bed. The type of reaction to be employed in a particular operation can be determined only after considering all these features.

Fluid-bed reactors are achieved where gas is passed through the reactor at a sufficient velocity to "fluidize" the catalyst particles. Because of this fluidized state, such beds have excellent heat conductivity and require only moderate amounts of heat transfer area. The feeds do not have to be well mixed, for this may take place within the bed. However, along with increased reactor size, a fluid bed tends to bypass reactant gas due to bubble formation. Grading of the catalyst is normally not possible due to the high degree of mixing in such a bed.

The present invention solves the problems normally associated with each type of bed, yet retains the advantages of both. In reactions involving several stages or steps, the present invention allows the combination of such steps in one reactor.

SUMMARY OF THE INVENTION

The invention is an apparatus for conducting a gas phase catalytic reaction comprising a fluid-bed reactor having a fluid-bed catalyst wherein one or more fixed-bed catalysts are located within the fluid bed.

The advantages of the invention are many. In processes requiring only one composition of catalyst, using the present invention allows all the advantages of both fixed and fluid-bed reactions. Catalyst inventories and reactor size may be reduced while still maintaining good temperature control and reactant mixing within the reactor.

Where a product is produced in a series of steps requiring two or more different catalysts, the advantages are even greater. For example, in the production of acrylic acid, the first step is typically the conversion of the reactants to acrolein in a fixed bed. This is followed by a second reactor using a fixed-bed catalyst to convert acrolein to acrylic acid. Using the present invention, such processes as this may be achieved in one reactor where both fixed and fluid-bed operations can take place. This reduces capital cost, simplifies the process, and allows the advantages of both fixed and fluid-bed operations.

The present invention has many useful applications in diverse fields such as hydrocarbon oxidation reactions, the production of acrylic or methacrylic acid, acrylonitrile, methacrylonitrile, methyl methacrylate, maleic anhydride, petroleum processing and coal conversion.

Central to the present invention is that the fixed-bed catalysts are located within the fluid bed. The catalyst located in the fixed bed do not move within the reactor. However, the fluid-bed particles also within the reactor move through the fixed bed in both an upward and downward direction. This movement of the fluid-bed catalyst achieves the beneficial results of good heat transfer and good mixing within the fixed catalyst bed.

The fixed-bed catalyst may be supported within the reactor on horizontal grids or screens, known in the art, with such an effective mesh size that prevents the fixed-bed particles from moving downward. As mentioned previously, fixed-bed catalysts are normally larger than fluid-bed catalysts. For the present invention, fixed-bed particles in the size range of 0.08 to 2.56 cm. effective diameter are preferred. This size allows good movement of the fluid-bed particles through the fixed-bed catalyst. While any fixed-bed particle shape may be used, for most applications particles which are approximately spherical in shape are preferred.

The support grids containing the fixed-bed catalyst may also have another grid or screen to limit the horizontal dispersement of the fixed-bed particles. Where needed, this would achieve a relatively uniform thickness of fixed-bed catalyst over the entire surface of the support grid. Without such a grid, the fixed-bed catalyst tends to build up against the reactor wall. Even so, the catalyst pellets rearrange themselves until a natural downcomer is formed.

The depth of the fixed-bed catalyst should be no more than two feet for any individual bed. This limitation allows for the movement of the fluid particles with a minimum of pressure drop. Preferred is a depth of about 0.05 to 1.9 ft.

The number of zones of fixed-bed catalysts will vary depending on the type of reaction. Only one bed may be necessary. For difficult reactions or those involving several reaction steps, the number of zones required may increase. In such reactions it is preferred that these zones be located in the upper portion of the fluidized bed. However, these zones may be located anywhere within the reactor with the exception of the very lowermost section. Also preferred is at least 0.1 feet of free space between the top of the fixed-bed catalyst level of a given bed and the lower level of the fixed bed immediately above it.

The fluid-bed catalysts have a range from about 5 to about 300 microns in diameter. The size and type of fluid-bed catalysts are known in the art for the various processes. In all cases, however, a zone of pure fluidized catalyst should be maintained in the lowermost section of the reactor to insure proper mixing of reactants.

The composition of the catalyst will vary depending on the type of reaction taking place. The fixed-bed catalyst may be the same composition as the fluid bed. Where additional reactions are taking place, the fixed-bed catalyst will contain one or more different catalyst. The fluid-bed catalyst may also contain different compositions than the fixed bed. It may also be a mixture of one or more catalyst compositions. Because of the invention's unique design, many variations of different catalysts may be used to optimize a certain reaction.

The fluidized bed may also contain sieve trays in the pure fluid regions of the reactor. The use of such trays in fluid-bed reactors are well known.

The reactor is any type normally associated with fluid-bed reactions. Typically the reactor consists of a disengaging zone where the catalyst is separated from the products, and a catalyst zone where the reaction takes place. The location of the fixed beds can be within either zone.

The reactor may additionally contain overflow downcomers to permit fluid catalyst to circulate from the region above the uppermost level of fixed-bed catalyst to some lower elevation in the reactor. The use of such devices will provide greater flow of fluid-bed particles through the fixed-bed zones.

The use of such known in the art devices as cyclones, filters and vertical or horizontal cooling coils within the reactor are also contemplated by the present invention.

The process conditions such as pressure and temperature will of course vary for the specific type of reaction. Where two steps of a reaction are combined, it may be advantageous to place the fixed-bed zones in the upper section of the fluidized bed at a different temperature than the rest of the reactor to help promote the desired reaction.

The catalyst circulation rate is apparently affected by the superficial linear vapor velocity. As this velocity increases, the catalyst circulation rate decreases. It has also been found that, depending upon the specific process variables, a certain amount of time is necessary for the system to stabilize and achieve a constant pressure drop through the total bed.

The invention thus achieves the desired benefits of fixed and fluid-bed operations without the disadvantages normally associated with each separately. This process improves heat transfer and reactor temperature control capabilities of fixed-bed reactors alone. In cases of multiple reactions, using the present invention allows for the elimination of one or more additional reactors, interstage lines, etc., thus greatly reducing the capital costs normally associated with the reactions.

DESCRIPTION OF THE DRAWING

In the drawing the view shows a fluidized bed of the invention having two fixed-bed catalyst trays.

Referring to the drawing, the fixed-fluid bed reactor 1 contains catalyst in the fluid state 2. This fluid catalyst is supported at the bottom of the reactor by grid 7.

Within the fluid bed are shown two trays 4. The number of trays, of course, will depend upon the specific reaction and the amount of fixed-bed catalyst desired.

The fixed-bed catalyst 3 rests on the trays. Screens 5 are provided to minimize the horizontal displacement of the fixed-bed catalyst caused by the movement of the fluid-bed catalyst through the trays.

A disengaging zone 6 is provided wherein the catalyst is separated from the reaction products.

Feed enters through line 8 at the bottom of the reactor. Although shown with one entry point, it is also common to provide a fluidizing feed separate from the other reactants. The feed passes through the reactor at such a velocity to fluidize the catalyst within the bed. The fluidized catalyst is in constant circulation within the reactor, passing through the fixed-bed catalyst in both directions.

Reaction of the feed takes place in both the fluidized catalyst and fixed-bed catalyst sections. Finally, the reaction products are removed from the top of the reactor above the disengaging zone of 9. In some fluidized-bed reactors, cyclones are used at the top of the reactor to separate the fluid-bed catalyst from the products.

SPECIFIC EMBODIMENT

Comparative Example A and Examples 1-3

A $1\frac{1}{2}''$ diameter 24" high sieve tray reactor was used to show the advantages of the present invention with respect to acrylic acid production. Approximately 550 cc of fluid-bed catalyst was used. This catalyst consisted of two types blended together; a first catalyst, 90% of an 82% $K_{0.1}Ni_{2.5}Co_{4.5}Fe_3Bi_1P_{0.5}Mo_{12}O_{50.3}$-18% $SiO_2$ useful for the conversion of propylene to acrolein and a second catalyst, 10% of a 62.5% $V_3W_{1.2}Mo_{12}O_{47.1}$-37.5% $SiO_2$ useful for the conversion of acrolein to acrylic acid. The particle size range was 5-149 microns, with average particle size about 55-60 microns.

For experiments 1-3 a fixed-bed catalyst of 20% $Cu_2Sn_{0.5}V_3W_{1.2}Mo_{12}O_{49.6}$-coated on inert 3/16" $Al_2O_3$ was prepared using known procedures, and 20 cc of this catalyst was placed on each support tray. Where more than one tray was used, the distance between the trays was approximately $1\frac{1}{2}''$. The depth of the catalyst on the trays was 35.5-36.5 mm. The fixed-bed catalyst was supported by a stainless steel screen of approximately 18 mesh, which in turn was supported by the trays.

The reactor was fed a stream of propylene, air and water in the mole ratio of 1/10/6. The reaction was run at atmospheric pressure while varying the temperature. The contact time was about 5.0 seconds at a gas velocity of 0.24-0.56 ft/sec.

Comparative Example A was run without the installation of the fixed-bed catalyst.

Example 1 shows the effect of the uppermost first tray in the catalyst reaction zone being the fixed-bed type.

Examples 2 and 3 show two fixed-bed trays being used, and the effect of varying the reaction temperature. The data for these experiments are shown in Table I. Single pass yield is defined as the moles of product obtained over the moles of propylene in the feed. The temperature shown is that of the middle of the reactor.

TABLE I

ACRYLIC ACID PRODUCTION

| Example | No. of Fixed Bed Trays | Temp. °C. | % Single Pass Yield Acrylic Acid | Acrolein |
|---|---|---|---|---|
| Comp. A | 0 | 332 | 28.7 | 58.0 |
| 1 | 1 | 332 | 51.1 | 26.9 |
| 2 | 2 | 332 | 64.1 | 9.7 |
| 3 | 2 | 349 | 69.8 | 3.1 |

It can be seen from these results that the present invention achieves high acrylic acid production in one reactor with combination fixed and fluid beds. The results are dramatic when compared to a blend of fluid-bed catalyst alone.

Comparative Example B and Examples 4–6

The same reactor and feed was used for Comparative Example B and Examples 4–6. However, the composition of the fluid catalyst was changed. A first fluid catalyst of 90% of a 50% $K_{0.1}Ni_{2.5}Co_{4.5}Fe_3Bi_1P_{0.5}Mo_{1.2}O_{50.3}$-50% $SiO_2$ was used, with the second fluid-bed catalyst remaining the same. The number of trays was varied from 1 to 6.

In Experiments 5 and 6 the upper fluid bed containing the fixed-bed zones was held at 360° to 377° C.

TABLE II

ACRYLIC ACID PRODUCTION

| Example | Fixed Bed Trays | Temp. °C. | % Single Pass Yield Acrylic Acid | Acrolein |
|---|---|---|---|---|
| Comp. B | 0 | 349 | 25.5 | 60.3 |
| 4 | 1 | 349 | 42.4 | 41.8 |
| 5 | 3 | 340 | 59.2 | 5.7 |
| 6 | 6 | 332 | 62.1 | 0.6 |

As can be seen by this table, the number of fixed-bed zones increases the desired reaction. Also, the present invention allows the reactor to be controlled non-isothermally for potentially better results.

EXAMPLE 7

A 1½" diameter sieve tray reactor was used to show the use of the present invention in the ammoxidation of propylene to acrylonitrile. A fixed-bed catalyst of 82.5% $K_{0.1}Ni_{2.5}Co_{4.5}Fe_3Bi_1P_{0.5}Mo_{12}O_{50.3}$-17.5% silica was supported on 3 trays within the reactor. A fluid-bed catalyst of the same composition but having 50% silica was used. The reactor was fed a stream of propylene, $NH_3$ and air in the ratio of 1/10.5/1.2. The reactor was run at 12 psig and 432° C. The results were an especially high conversion to acrylonitrile and the elimination of $NH_3$ breakthrough in the reactor effluent.

We claim:

1. In a process for the gas phase catalytic oxidation of propylene to acrylic acid, the improvement comprising conducting said oxidation in a fluid-bed reactor vessel, said vessel having a bed of catalyst particles contained therein and maintained in a fluidized state by the flow of reactant gases therethrough, and having within said fluidized catalyst particle bed above the point necessary for the mixing of the reactant gases, one or more fixed-bed catalysts retained within one or more fixed-bed catalyst supports, said supports having means for retaining a fixed-bed catalyst on top of the support, and means for allowing the fluidized catalyst particles to circulate through said fixed-bed catalyst.

2. In a process for the gas phase catalytic oxidation of isobutylene to methacrylic acid the improvement comprising conducting said oxidation in a fluid-bed reactor vessel, said vessel having a bed of catalyst particles contained therein and maintained in a fluidized state by the flow of reactant gases therethrough, and having within said fluidized catalyst particle bed above the point necessary for the mixing of the reactant gases, one or more fixed-bed catalysts retained within one or more fixed-bed catalyst supports, said supports having means for retaining a fixed-bed catalyst on top of the support, and means for allowing the fluidized catalyst particles to circulate through said fixed-bed catalyst.

* * * * *